US010117764B2

(12) United States Patent
Caldarise et al.

(10) Patent No.: US 10,117,764 B2
(45) Date of Patent: Nov. 6, 2018

(54) BARE METAL STENT WITH DRUG ELUTING RESERVOIRS HAVING IMPROVED DRUG RETENTION

(75) Inventors: Salvatore G. Caldarise, Belle Mead, NJ (US); Carl J. Evens, Branchburg, NJ (US)

(73) Assignee: CARDINAL HEALTH SWITZERLAND 515 GMBH, Bar Zug (CH)

(*) Notice: Subject to any disclaimer, the term of this patent is extended or adjusted under 35 U.S.C. 154(b) by 607 days.

(21) Appl. No.: 12/915,166

(22) Filed: Oct. 29, 2010

(65) Prior Publication Data

US 2012/0109284 A1    May 3, 2012

(51) Int. Cl.
*A61F 2/82*      (2013.01)
*A61F 2/91*      (2013.01)

(52) U.S. Cl.
CPC ........ *A61F 2/91* (2013.01); *A61F 2250/0068* (2013.01); *Y10T 29/4998* (2015.01)

(58) Field of Classification Search
CPC ..................................... A61F 2/06; A61F 2/82
USPC ..................................... 623/1.15, 1.16, 1.42
See application file for complete search history.

(56) References Cited

U.S. PATENT DOCUMENTS 6,656,162 B2 * 12/2003 Santini et al. ................. 604/191
6,764,507 B2    7/2004 Shanley et al.

| 2002/0017503 A1 * | 2/2002 | Banas ............. A61F 2/91 |
| | | 219/69.11 |
| 2003/0105512 A1 | 6/2003 | Kanesaka |
| 2009/0076591 A1 | 3/2009 | Girton et al. |

FOREIGN PATENT DOCUMENTS

| JP | 2008-504926 A | 6/2005 |
| JP | 2008504926 A | 2/2008 |

OTHER PUBLICATIONS

International Searching Authority, Transmittal of the International Search Report and the Written Opinion dated Jan. 2, 2012.
Fischman, D., et al. "A Randomized Comparison of Coronary-Stent Placement and Balloon Angioplasty in the Treatment of Coronary Artery Disease", The New England Journal of Medicine, vol. 331:496-501 (1994).
Serruys, P., et al. "A Comparison of Balloon-Expandable-Stent Implantation with Balloon Angioplasty in Patients with Coronary Artery Disease", New England Journal of Medicine, vol. 331:489-495 (1994).

(Continued)

*Primary Examiner* — Matthew Schall
(74) *Attorney, Agent, or Firm* — Dergosits & Noah LLP; Todd A. Noah (57) ABSTRACT

Implantable medical devices may be utilized to locally delivery one or more drugs or therapeutic agents to treat a wide variety of conditions, including the treatment of the biological organism's reaction to the introduction of the implantable medical device. These therapeutic agents may be released under controlled and directional conditions from a stent having reservoirs so that the one or more therapeutic agents reach the correct target area, for example, the surrounding tissue. Features may be incorporated into the walls and bases of these reservoirs to improve securement of the drug construct.

8 Claims, 5 Drawing Sheets

(56) References Cited

OTHER PUBLICATIONS

Office Action dated Aug. 26, 2015, for corresponding Canadian Patent Application No. 2,814,653.
Office Action dated Jan. 5, 2016, for Japan Patent Application No. 2013-536642.
Decision on Rejection dated Oct. 27, 2016 in corresponding Chinese Patent Application No. 201180052965.X, 9 pages.
Decision of Reasons for Refusal dated Nov. 29, 2016 in corresponding Japanese Patent Application No. 2013-536642, 5 pages.
Office Action dated Jun. 16, 2015 for corresponding Japan Patent Application No. 2013-536642.
Office Action dated Jul. 2, 2015 for corresponding China Patent Application No. 201180052965.X.
Office Action dated Oct. 11, 2014 for corresponding China Patent Application No. 201180052965.X.
Chinese Notice of Reexamination Report from corresponding Chinese Patent Application 201180052965.X, dated Jun. 23, 2017, pp. 1-7.
European Examination Report from corresponding European Patent Application 11770627.5, dated Apr. 13, 2017, pp. 1-4.

\* cited by examiner

BARE METAL STENT WITH DRUG ELUTING RESERVOIRS HAVING IMPROVED DRUG RETENTION

BACKGROUND OF THE INVENTION

1. Field of the Invention

The present invention relates to the local administration of therapeutic agents and/or therapeutic agent combinations for the prevention and treatment of vascular disease, and more particularly to intraluminal medical devices having reservoirs with retention features for the local delivery of therapeutic agents and/or therapeutic agent combinations.

2. Discussion of the Related Art

Many individuals suffer from circulatory disease caused by a progressive blockage or narrowing of the blood vessels that perfuse the heart and other major organs. More severe blockage of blood vessels in such individuals often leads to hypertension, ischemic injury, stroke, or myocardial infarction. Atherosclerotic lesions, which limit or obstruct coronary blood flow, are the major cause of ischemic heart disease. Alternately, spontaneous rupture of inflammatory atherosclerotic lesions or vulnerable plaque may lead to intermittent or complete thrombotic occlusion of an artery causing ischemic injury such as stroke and/or acute myocardial infarction. Percutaneous transluminal coronary angioplasty is a medical procedure whose purpose is to increase blood flow through an artery. Percutaneous transluminal coronary angioplasty is the predominant treatment for coronary vessel stenosis. The increasing use of this procedure is attributable to its relatively high success rate and its minimal invasiveness compared with coronary bypass surgery. A limitation associated with percutaneous transluminal coronary angioplasty is the abrupt closure of the vessel, which may occur immediately after the procedure and restenosis, which occurs gradually following the procedure. Additionally, restenosis is a chronic problem in patients who have undergone saphenous vein bypass grafting. The mechanism of acute occlusion appears to involve several factors and may result from vascular recoil with resultant closure of the artery and/or deposition of blood platelets and fibrin along the damaged length of the newly opened blood vessel.

Restenosis after percutaneous transluminal coronary angioplasty is a more gradual process initiated by vascular injury. Multiple processes, including thrombosis, inflammation, growth factor and cytokine release, cell proliferation, cell migration and extracellular matrix synthesis each contribute to the restenotic process.

Unlike systemic pharmacologic therapy, stents have proven useful in significantly reducing restenosis. Typically, stents are balloon-expandable slotted metal tubes (usually, but not limited to, stainless steel), which, when expanded within the lumen of an angioplastied coronary artery, provide structural support through rigid scaffolding to the arterial wall. This support is helpful in maintaining vessel lumen patency. In two randomized clinical trials, stents increased angiographic success after percutaneous transluminal coronary angioplasty, by increasing minimal lumen diameter and reducing, but not eliminating, the incidence of restenosis at six months (Serruys et al., 1994; Fischman et al., 1994). In addition, stents have become the treatment of choice for revascularization of a thrombosed coronary artery (acute myocardial infarction) in which rapid restoration of blood flow to ischemic myocardial tissue is the primary determinant of long term clinical benefit. Full restoration of coronary blood flow with a stent within 6 hours of presentation of symptoms, and preferably under 3 hour, has been shown to produce superior clinical outcomes over administration of a thrombolytic agent (tPA, streptokinase, etc.) to dissolve a thrombotic occlusion.

Stents utilized for the local delivery of rapamycins, including sirolimus, everolimus and other rapamycin analogs and derivatives (mTOR inhibitors), have proved more successful in significantly reducing restenosis and related complications following percutaneous transluminal angioplasty and other similar arterial/venous procedures than bare metal stents. Rapamycins may be incorporated onto or affixed to the stent in a number of ways. For example, the rapamycins may be incorporated into a polymeric matrix and then affixed to the surface of the stent by any suitable means. The rapamycins elute from the polymeric matrix over a given period of time and into the surrounding tissue.

Additionally, heparin coating of stents appears to have the added benefit of producing a reduction in sub-acute thrombosis after stent implantation. Thus, sustained mechanical expansion of a stenosed coronary artery with a stent has been shown to provide some measure of restenosis prevention, and the coating of stents with rapamycins and heparin has demonstrated both the feasibility and the clinical usefulness of delivering drugs locally, at the site of injured tissue.

Drug elution achieved by coated stents has been a recent development in this field. However, further development in stent technology has resulted in stents comprising drug eluting reservoirs. Stents with drug eluting reservoirs have enabled more flexibility and options in drug choice, deliverability, and treatments. With reservoir based drug eluting stents the drug component is typically located within the reservoir, which is in contrast to coated stents where the drug and polymer are formulated into a coating which is applied to portions of the stent surface. As stent designs continue to be refined and are made smaller and more flexible, and the service conditions for which these stents are utilized becomes more demanding, securement of the drug component within the reservoir will become more important and more difficult to reliably achieve. In addition to mechanical forces which may be imparted to the reservoir during delivery of the stent, the act of stent crimping and expansion may result in additional mechanical loading to the inlays within the reservoir of the stent.

Accordingly, there exists a need for a reservoir based drug eluting stent having improved reservoir features for the securement of the drugs or other therapeutic agents therein thereby enabling the drug inlay to remain unaffected during manufacture, preparation, delivery and available for the prevention and treatment of vascular injury as described above.

SUMMARY OF THE INVENTION

The reservoir based drug eluting stent of the present invention overcomes the limitations of the prior art devices as briefly set forth above.

In accordance with one aspect, the present invention is directed to a bare metal stent with drug eluting reservoirs for implantation into a tubular organ of a living organism. The present invention is directed to a bare metal stent with drug eluting reservoirs for implantation into a tubular organ of a living organism comprising an elongated, substantially tubular structure having a luminal surface and an abluminal surface, the elongated, substantially tubular structure including a plurality of interconnected elements, a portion of which comprise at least one reservoir; at least one retention and securement feature operatively associated with the at least one reservoir; and an inlay, including at least one of a polymer and therapeutic agent, positioned within the at least one reservoir, the at least one retention and securement feature anchoring the inlay within the at least one reservoir.

In accordance with another aspect, the present invention is directed to a method for creating a bare metal stent with drug eluting reservoirs having improved securement. The method comprising the steps of providing an elongated, substantially tubular structure having a luminal surface and an abluminal surface, the elongated, substantially tubular structure including a plurality of interconnected elements, a portion of which comprise at least one reservoir, wherein the at least one reservoir having at least one retention and securement feature; introducing a liquid formulation of at least one of a polymer and therapeutic agent to be received into the at least one reservoir such that the liquid formulation fully engages with the retention and securement feature of the reservoir; and curing the liquid formulation resulting in an inlay that is interlocked with the retention and securement feature.

The stent of the present invention comprises a unique design as briefly described above and may be formed from any suitable material, including a cobalt-chromium alloy. The stent is designed to maintain vessel patency and to locally deliver a rapamycin or other therapeutic agent or combination of agents to the surrounding arterial tissue for the prevention and treatment of vascular disease, including restenosis. The therapeutic agent is incorporated into a polymeric matrix, preferably along with a stabilizing agent such as butylated hydroxyl toluene and deposited into reservoirs in the stent. Each reservoir in the stent is filled with a solution comprising the therapeutic agent, the polymer, the stabilizing agent and the solvent. The filling process includes a series of deposition steps followed by drying steps to remove the solvent. The construct of each reservoir may function to minimize the elution of the therapeutic agent into the bloodstream while maximizing it into the arterial tissue surrounding the stent or alternatively maximize elution into the bloodstream while minimizing it into the arterial tissue, or when desired, may be a combination of both luminal and abluminal eluting reservoirs maximizing elution into both the bloodstream and arterial tissue.

The stent of the present invention may provide for the controlled, sustained and local delivery of the therapeutic agent directly into the surrounding tissue with minimal loss into the blood or alternatively directly into the bloodstream with minimal loss into the surrounding tissue, or directly into both the bloodstream and tissue while improving the fixation of the combined therapeutic agent inlay to that of the reservoir. The stent is preferably fabricated from a cobalt-chromium alloy that is less brittle and has enhanced ductility and toughness as well as increased durability as compared to stents fabricated from other materials.

Reservoir eluting stents offer a number of advantages over standard surface coated drug eluting stents. For example, reservoirs protect the polymer and drug matrix or composition deposited therein from mechanical disruption during passage through the tortuous anatomy and highly calcified lesions that may cause delaminating of standard surface coated stents. Reservoirs allow higher drug loading capacity and higher drug to polymer ratios because the polymers in the reservoir are not subject to the elongation and deformation associated with polymer surface coatings. Reservoirs also require less polymer mass than conventional surface coatings and can reduce strut thickness by ten to thirty microns thereby improving both the flexibility of the stent as well as reducing the overall profile of the device. Reservoirs also make it easier to deliver multiple drugs and or therapeutic agents from a stent with independent release profiles and to treat the metallic surfaces of the stent without affecting its drug and polymer attributes. Furthermore, reservoirs provide greater flexibility and options as it relates to providing selective directional delivery and positional and/or directional localized delivery. In addition, reservoirs may offer better vessel biocompatibility by providing a stent surface that is predominantly bare metal with virtually no polymer contacting the vessel wall on implantation. This is true given the meniscus of the composition within the reservoirs and the less than complete filling of the available reservoir as is explained in detail subsequently. By incorporation of a fixation feature in accordance with the present invention, one can secure and maintain the fixation of the therapeutic agent inlay to that of the reservoir for the complete service life of the stent, or in cases of absorbable or resorbable inlays, until the therapeutic agent inlay is completely absorbed or resorbed. During delivery of the stent to the targeted area and upon deployment of the stent, the stent and resulting inlays may be subject to loading and deformations which may impact the fixation of the drug inlay. The use of features in the reservoirs may provide an additional level of fixation resulting in the inlay being securely fixed and remain being fixed throughout the service life of the stent.

BRIEF DESCRIPTION OF THE DRAWINGS

The foregoing and other features and advantages of the invention will be apparent from the following, more particular description of preferred embodiments of the invention, as illustrated in the accompanying drawings.

DETAILED DESCRIPTION OF THE PREFERRED EMBODIMENTS

The drug/drug combinations and delivery devices of the present invention may be utilized to effectively prevent and treat vascular disease. While exemplary embodiments of the invention will be described with respect to the treatment of restenosis and related complications following percutaneous transluminal coronary angioplasty, it is important to note that the local delivery of drug/drug combinations may be utilized to treat a wide variety of conditions utilizing any number of medical devices, or to enhance the function and/or life of the device. For example, intraocular lenses, placed to restore vision after cataract surgery is often compressed by the formation of a secondary cataract. The latter is often a result of cellular overgrowth on the lens surface and can be potentially minimized by combining a drug or drugs with the device. Other medical devices which often fail due to tissue in-growth or accumulation of proteinaceous material in, on and around the device such as shunts for hydrocephalus, dialysis grafts, colostomy bag attachment devices, ear drainage tubes, leads for pace makers and implantable defibrillators can also benefit from the device-drug combination approach. Devices which serve to improve the structure and function of tissue or organ may also show benefits when combined with the appropriate agent or agents. For example, improved osteointegration of orthopedic devices to enhance stabilization of the implanted device could potentially be achieved by combining it with agents such as bone-morphogenic protein. Similarly other surgical devices, sutures, staples, anastomosis devices, vertebral disks, bone pins, suture anchors, hemostatic barriers, clamps, screws, plates, clips, vascular implants, tissue adhesives and sealants, tissue scaffolds, various types of dressings, bone substitutes, intraluminal devices, and vascular supports could also provide enhanced patient benefit using this drug-device combination approach. Perivascular wraps may be particularly advantageous, alone or in combination with other medical devices. The perivascular wraps may supply additional drugs to a treatment site. Essentially, any type of medical device may be coated or loaded in some fashion with a drug or drug combination which enhances treatment over that of the singular use of the device or pharmaceutical agent alone.

In addition to various medical devices, the reservoirs included with these devices may be used to deliver therapeutic and pharmaceutic agents including: anti-proliferative/antimitotic agents including natural products such as vinca alkaloids (i.e. vinblastine, vincristine, and vinorelbine), paclitaxel, epidipodophyllotoxins (i.e. etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagine); antiplatelet agents such as G(GP) $II_b/III_a$ inhibitors and vitronectin receptor antagonists; anti-proliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nirtosoureas (carmustine (BCNU) and analogs, streptozocin), trazenes—dacarbazinine (DTIC); anti-proliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine {cladribine}); platinum coordination complexes (cisplatin, carboplatin), procarbazine, hydroxyurea, mitotane, aminoglutethimide; hormones (i.e. estrogen); anti-coagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory; antisecretory (breveldin); anti-inflammatory: such as adrenocortical steroids (cortisol, cortisone, fludrocortisone, prednisone, prednisolone, 6α-methylprednisolone, triamcinolone, betamethasone, and dexamethasone), non-steroidal agents (salicylic acid derivatives i.e. aspirin; para-aminophenol derivatives i.e. acetaminophen; indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressives: (cyclosporine, tacrolimus (FK-506), sirolimus (rapamycin), azathioprine, mycophenolate mofetil); angiogenic agents: vascular endothelial growth factor (VEGF), fibroblast growth factor (FGF); angiotensin receptor blockers; nitric oxide donors; antisense oligionucleotides and combinations thereof; cell cycle inhibitors, mTOR inhibitors, and growth factor receptor signal transduction kinase inhibitors; retenoids; cyclin/CDK inhibitors; HMG co-enzyme reductase inhibitors (statins); and protease inhibitors.

The local delivery of drug/drug combinations from a stent has the following advantages; namely, the prevention of vessel recoil and remodeling through the scaffolding action of the stent and the prevention of multiple components of neointimal hyperplasia or restenosis as well as a reduction in inflammation and thrombosis. This local administration of drugs, agents or compounds to stented coronary arteries may also have additional therapeutic benefit. For example, higher tissue concentrations of the drugs, agents or compounds may be achieved utilizing local delivery, rather than systemic administration. In addition, reduced systemic toxicity may be achieved utilizing local delivery rather than systemic administration while maintaining higher tissue concentrations. Also in utilizing local delivery from a stent rather than systemic administration, a single procedure may suffice with better patient compliance. An additional benefit of combination drug, agent, and/or compound therapy may be to reduce the dose of each of the therapeutic drugs, agents or compounds, thereby limiting their toxicity, while still achieving a reduction in restenosis, inflammation and thrombosis. Local stent-based therapy is therefore a means of improving the therapeutic ratio (efficacy/toxicity) of anti-restenosis, anti-inflammatory, anti-thrombotic drugs, agents or compounds.

There are a multiplicity of different stents and varying geometries of reservoirs that may be utilized following percutaneous transluminal coronary angioplasty. Although any number of stents may be utilized in accordance with the invention, for simplicity, a limited number of stents will be described in exemplary embodiments of the present invention. The skilled artisan will recognize that any number of stents and varying reservoir geometries may be utilized in connection with the invention. In addition, as stated above, other medical devices may be utilized. Multiple approaches in securement of the inlay structure to that of the reservoir may also be utilized alone or in combination in accordance with the invention.

A stent is commonly used as a tubular structure left inside the lumen of a duct to relieve an obstruction. Commonly, stents are inserted into the lumen in a non-expanded form and are then expanded autonomously, or with the aid of a second device in situ. A typical method of expansion occurs through the use of a catheter-mounted angioplasty balloon which is inflated within the stenosed vessel or body passageway in order to shear and disrupt the obstructions associated with the wall components of the vessel and to obtain an enlarged lumen. There also exists stents fabricated from self-expanding materials such as nitinol. These stents expand upon their own accord when the sheath restraining them is removed.

Figure 1:
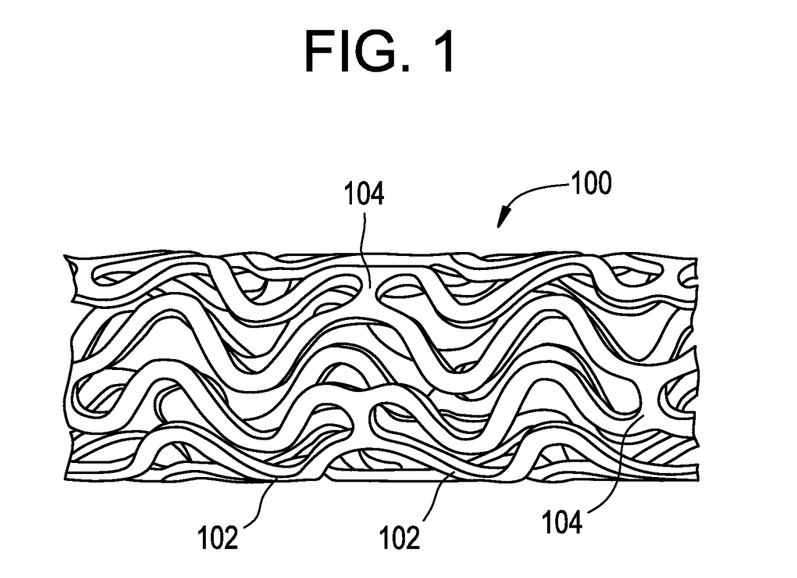
FIG. 1 is a view along the length of a stent (ends not shown) prior to expansion showing the exterior surface of the stent and the characteristic banding pattern.

FIG. 1 illustrates an exemplary stent 100 which may be utilized in accordance with an exemplary embodiment of the invention. The expandable cylindrical stent 100 comprises a fenestrated structure for placement in a blood vessel, duct or lumen to hold the vessel, duct or lumen open, more particularly for protecting a segment of artery from restenosis after angioplasty. The stent 100 may be expanded circumferentially and maintained in an expanded configuration that is circumferentially or radially rigid. The stent 100 is axially flexible and when flexed at a band, the stent 100 avoids any externally protruding component parts.

The stent 100 generally comprises first and second ends with an intermediate section therebetween. The stent 100 has a longitudinal axis and comprises a plurality of longitudinally disposed bands 102, wherein each band 102 defines a generally continuous wave along a line segment parallel to the longitudinal axis. A plurality of circumferentially arranged links 104 maintain the bands 102 in a substantially tubular structure. Essentially, each longitudinally disposed band 102 is connected at a plurality of periodic locations, by a short circumferentially arranged link 104 to an adjacent band 102. The wave associated with each of the bands 102 has approximately the same fundamental spatial frequency in the intermediate section, and the bands 102 are so disposed that the wave associated with them are generally aligned so as to be generally in phase with one another. As illustrated in the figure, each longitudinally arranged band 102 undulates through approximately two cycles before there is a link to an adjacent band 102.

The stent 100 may be fabricated utilizing any number of methods. For example, the stent 100 may be fabricated from a hollow or formed stainless steel tube that may be machined or fabricated using lasers, electric discharge milling, chemical etching or other means. The stent 100 is inserted into the body and placed at the desired site in an unexpanded form. In one exemplary embodiment, expansion may be affected in a blood vessel by a balloon catheter, where the final diameter of the stent 100 is a function of the diameter of the balloon catheter used as well as the design (expansion ratio) of the stent.

It should be appreciated that a stent 100 in accordance with the invention may be embodied in a shape-memory material, including, for example, an appropriate alloy of nickel and titanium or stainless steel. Structures formed from stainless steel may be made self-expanding by configuring the stainless steel in a predetermined manner, for example, by twisting it into a braided configuration. In this embodiment after the stent 100 has been formed it may be compressed so as to occupy a space sufficiently small as to permit its insertion in a blood vessel or other tissue by insertion means, wherein the insertion means include a suitable catheter, or flexible rod. On emerging from the catheter, the stent 100 may be configured to expand into the desired configuration where the expansion is automatic in the case of shape-memory alloys or triggered by a change in pressure, temperature or electrical stimulation or augmented by devices such as balloon catheters when the stents are fabricated from non self-expanding materials.

Figure 2:
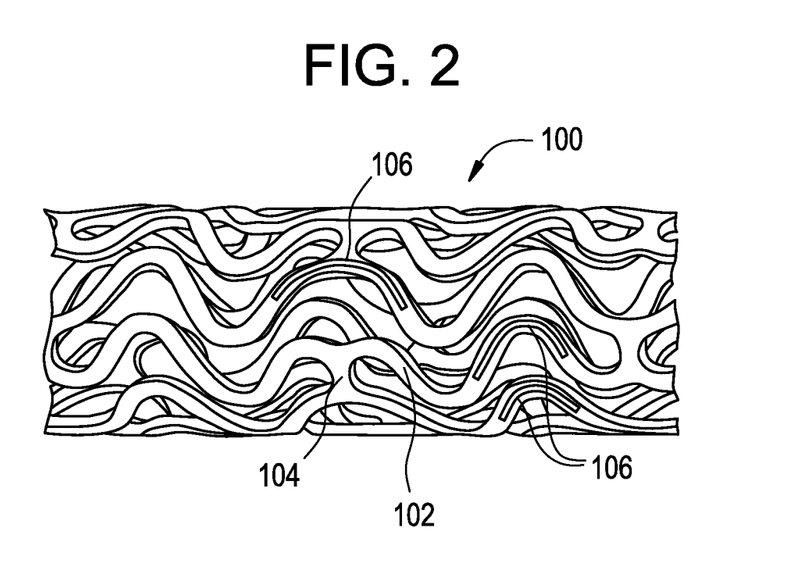
FIG. 2 is a perspective view along the length of the stent of FIG. 1 which is modified to include reservoirs.

FIG. 2 illustrates an exemplary embodiment of the invention utilizing the stent 100 illustrated in FIG. 1. As illustrated, the stent 100 may be modified to comprise one or more reservoirs 106. Each of the reservoirs 106 may be opened or closed as desired. These reservoirs 106 may be specifically designed to hold the drug/drug combinations to be delivered. Regardless of the design of the stent 100, it is preferable to have the drug/drug combination dosage applied with enough specificity and a sufficient concentration to provide an effective dosage for the condition to be treated. In this regard, the reservoir size in the bands 102 is preferably sized to adequately apply the drug/drug combination dosage at the desired location and in the desired amount. However, it is important to note that the stent illustrated in FIG. 1 may also be utilized to delivery drug/drug combinations. For example, the surface of the stent may be coated directly with drug/drug combinations or as part of a polymeric matrix affixed to the surface of the stent. In other words, the stent surface coating is or acts as the drug delivery depot which provides additional options and configurations when combining the surface coating delivery with that of reservoir based delivery.

Figure 3:
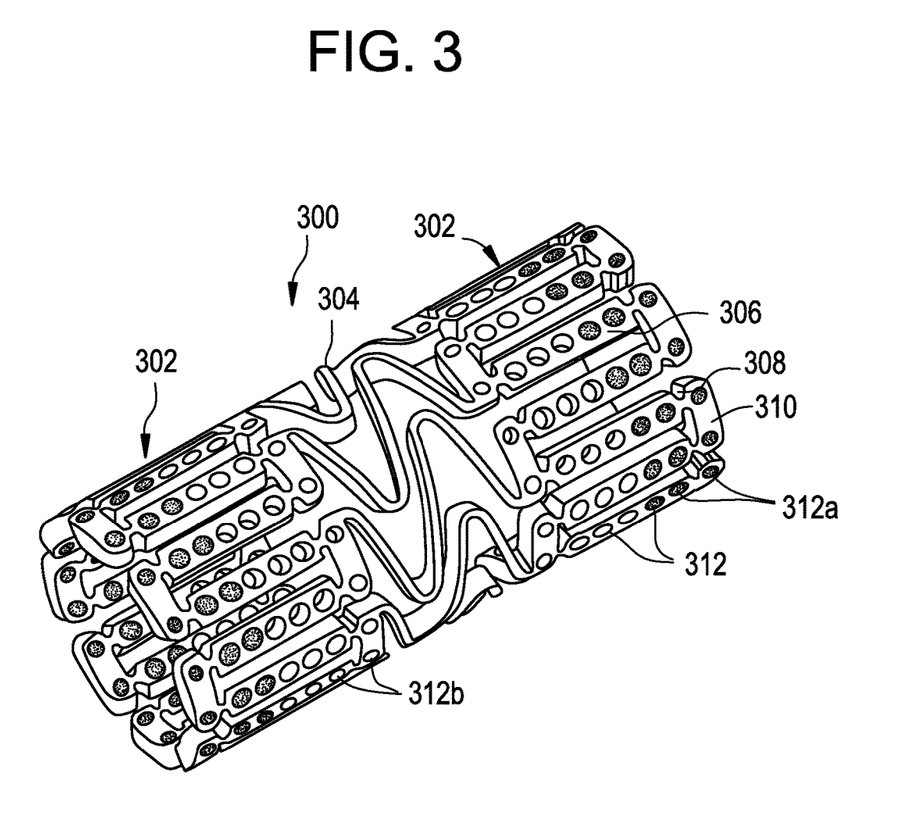
FIG. 3 is an isometric view of an expandable medical device of an alternative design having reservoirs with a beneficial agent at the ends thereof.

FIG. 3 illustrates an alternate exemplary expandable medical device having a plurality of holes containing a beneficial agent for delivery to tissue by the expandable medical device. The expandable medical device 300 illustrated in FIG. 3 is cut from a tube of material to form a cylindrical expandable device. The expandable medical device 300 includes a plurality of cylindrical sections 302 interconnected by a plurality of bridging elements 304. The bridging elements 304 allow the tissue supporting device to bend axially when passing through the torturous path of vasculature to a deployment site and allow the device to bend axially when necessary to match the curvature of a lumen to be supported. Each of the cylindrical sections 302 is formed by a network of elongated struts 306 which are interconnected by ductile hinges 308 and circumferential struts 310. During expansion of the medical device 300 the ductile hinges 308 deform while the struts 306 are not deformed. Further details of one example of the expandable medical device are described in U.S. Pat. No. 6,241,762 which is incorporated herein by reference in its entirety.

As illustrated in FIG. 3, the elongated struts 306 and circumferential struts 310 include openings 312, some or all of which contain a beneficial agent for delivery to the lumen in which the expandable medical device is implanted. In addition, other portions of the device 300, such as the bridging elements 304, may include openings. Preferably, the openings 312 are provided in non-deforming portions of the device 300, such as the struts 306, so that the openings are non-deforming and the beneficial agent is delivered without risk of being fractured, expelled, or otherwise damaged during expansion of the device. By incorporating additional securement features as described below in accordance with the present invention, this potential risk is significantly further decreased. A further description of one example of the manner in which the beneficial agent may be loaded within the openings 312 is described in U.S. Pat. No. 6,764,507, filed Sep. 7, 2001, which is incorporated herein by reference in its entirety.

The exemplary embodiments of the invention illustrated may be further refined by using Finite Element Analysis and/or other techniques to optimize the deployment of the beneficial agents within the openings 312. Basically, the shape and location of the openings 312, may be modified to maximize the volume of the voids while preserving the relatively high strength and rigidity of the struts with respect to the ductile hinges 308. According to one preferred exemplary embodiment of the present invention, the openings have an area of at least $5 \times 10^{-6}$ square inches, and preferably at least $7 \times 10^{-6}$ square inches. Typically, the openings are filled about fifty percent to about ninety-five percent full of beneficial agent.

The exemplary stent described herein comprises a cobalt-chromium alloy. In accordance with the present invention, a cobalt-chromium alloy such as L605 may be utilized to fabricate the stent. A traditional cobalt-based alloy such as L605 (i.e., UNS R30605) which is also broadly utilized as an implantable, biocompatible device material may comprise chromium (Cr) in the range from about 19 to 21 weight percent, tungsten (W) in the range from about 14 to 16 weight percent, nickel (Ni) in the range from about 9 to 11 weight percent, iron (Fe) in the range up to 3 weight percent, manganese (Mn) in the range up to 2 weight percent, silicon (Si) in the range up to 1 weight percent, with cobalt (cobalt) comprising the balance (approximately 49 weight percent) of the composition.

Alternately, another traditional cobalt-based alloy such as Haynes 188 (i.e., UNS R30188) which is also broadly utilized as an implantable, biocompatible device material may comprise nickel (Ni) in the range from about 20 to 24 weight percent, chromium (Cr) in the range from about 21 to 23 weight percent, tungsten (W) in the range from about 13 to 15 weight percent, iron (Fe) in the range up to 3 weight percent, manganese (Mn) in the range up to 1.25 weight percent, silicon (Si) in the range from about 0.2 to 0.5 weight percent, lanathanum (La) in the range from about 0.02 to 0.12 weight percent, boron (B) in the range up to 0.015 weight percent with cobalt (Co) comprising the balance (approximately 38 weight percent) of the composition.

In general, elemental additions such as chromium (Cr), nickel (Ni), tungsten (W), manganese (Mn), silicon (Si) and molybdenum (Mo) were added to iron- and/or cobalt-based alloys, where appropriate, to increase or enable desirable performance attributes, including strength, the ability to machine and corrosion resistance within clinically relevant usage conditions.

In accordance with exemplary embodiments of the present invention, single beneficial agents may be loaded into the reservoirs or holes in the stent or coated onto the surface thereof or combinations of both in a single device. In addition, multiple beneficial agents may be loaded into the reservoirs or holes in the stent or coated onto the surface thereof. The use of reservoirs or holes for drug or agent release as described above with respect to FIG. 3 makes using different beneficial agents easier as well as offering a number of advantages as set forth herein. Different beneficial agents comprising different drugs may be disposed in different openings in the stent. This allows the delivery of two or more beneficial agents from a single stent in any desired delivery pattern and with independent drug release rate profiles. Alternately, different beneficial agents comprising the same drug in different concentrations may be disposed in different openings. This allows the drug to be uniformly distributed to the tissue with a non-uniform device structure.

The two or more different beneficial agents provided in the devices described herein may comprise (1) different drugs; (2) different concentrations of the same drug; (3) the same drug with different release kinetics, i.e., different matrix erosion rates; (4) different forms of the same drug; or (5) any combination of the above. Examples of different beneficial agents formulated comprising the same drug with different release kinetics may use different carriers to achieve the elution profiles of different shapes. Some examples of different forms of the same drug include forms of a drug having varying hydrophilicity or lipophilicity. These various combinations may each be augmented with an optional drug containing surface coating providing additional options and/or constructs.

In addition to the use of different beneficial agents in different openings to achieve different drug concentrations at different defined areas of tissue or in the bloodstream, the loading of different beneficial agents in different openings may be used to provide a more even spatial distribution of the beneficial agent delivered in instances where the expandable medical device has a non-uniform distribution of openings in the expanded configuration. The use of different drugs in different openings in an interspersed or alternating manner allows the delivery of two different drugs which may not be deliverable if combined within the same polymer/drug matrix composition. For example, the drugs themselves may interact in an undesirable way. Alternatively, the two drugs may not be compatible with the same polymers for formation of the matrix or with the same solvents for delivery of the polymer/drug matrix into the openings.

Given that the openings in the stent of FIG. 3 are through holes, the construct of the loading of the openings with the one or more beneficial agents may be utilized to determine the direction of the release of the one or more beneficial agents, for example, predominantly to the luminal or abluminal side of the expandable medical device. In addition to the delivery of different beneficial agents to the mural or abluminal side of the expandable medical device for treatment of the vessel wall, beneficial agents may be delivered to the luminal side of the expandable medical device to prevent or reduce thrombosis or to directly and locally deliver agents into the bloodstream for the treatment of organs downstream of the implantation side as discussed in detail subsequently. Drugs which are delivered into the blood stream from the luminal side of the device may be located at a distal end of the device or at desired specified regions of the device.

The methods for loading different beneficial agents into different openings in an expandable medical device may include known techniques such as dipping and coating, and also known piezoelectric micro-jetting techniques. Micro-injection devices may be computer controlled to deliver precise amounts of two or more liquid beneficial agents to precise locations on the expandable medical device in a known manner. For example, a dual agent jetting device may deliver two agents simultaneously or sequentially into the openings. When the beneficial agents are loaded into through openings in the expandable medical device, a luminal side of the through openings may be blocked during loading by a resilient mandrel allowing the beneficial agents to be delivered in liquid form, such as with a solvent. Being delivered as a liquid allows the composition to flow around and/or into the securement feature thereby securing the inlay upon curing. The beneficial agents may also be loaded by manual injection devices.

The composition in accordance with the present invention is loaded into the reservoirs in a sequential series of steps, including depositing a fluid filling solution composition into the reservoirs, achieving interdigitization of the solution composition to that of the reservoir and securement feature and evaporating a majority, if not substantially all, of the filling solution solvent. Having no solvent in the final composition is the ideal situation. It should be appreciated that any suitable deposit process may be utilized as described herein. The composition in accordance with the present invention as described above is the solid materials that remain in and are securely attached to the reservoir after removal of substantially all or preferably all of the solvent from the filling solution composition.

The exemplary fluid compositions used to form the solid composition comprising sirolimus as the therapeutic agent include a bioresorbable or bioabsorbable polymer, preferably a poly(lactide-co-glycolide), PLGA, polymer, a suitable solvent such as dimethyl sulfoxide, DMSO, or N-methyl pyrrolidinone, NMP, sirolimus and optionally a stabilizer or anti-oxidant such as butylated hydroxy toluene or BHT. An alternate spelling for BHT is butylated hydroxtoluene. Preferably, at least one of the fluid filling solution compositions utilized in a deposition step to create the final sirolimus compositions in the stent reservoirs comprises BHT.

Alternatives for BHT include butylated hydroxyl anisole, BHA, gallate esters such as propyl gallate or ascorbate esters such as palmitoyl ascorbate. BHT is preferred based upon its high level of effectiveness in stabilizing sirolimus, its low level toxicity and its hydrophobicity. BHT elutes from the reservoirs at approximately the same rate as sirolimus and as such there is preferably BHT present with the sirolimus. Alternatives for DMSO and NMP include dimethyl acetomide (DMAc) or dimethyl formamide (DMF). DMSO is preferred because sirolimus is more stable in the presence of DMSO.

Each sequential fluid composition that is deposited may comprise the same ingredients or constituents, or sequential filling solutions may be prepared from filling solutions comprising different ingredients or constituents. Preferably, the first series of filling solution deposits comprise only polymer and solvent, which, as described above, are dried after each filling step. This part of the process results in the formation of a base structure. In a preferred exemplary, five separate base filling steps are performed with a drying period of one hour at fifty-five degrees C. between each filling step to remove solvent from the composition. Once the base structure is formed, subsequent solutions comprising polymer, solvent, sirolimus and BHT are added and are also dried after each filling step. In a preferred exemplary, four separate drug containing filling steps are performed with a drying period of one hour at fifty-five degrees C. between each filling step to remove solvent from the drug containing composition. After the final filing step, the stent is dried for a period of twenty-four hours at fifty-five degrees C. This manufacturing sequence will create a reservoir composition in which there is a lower concentration of sirolimus in the area of the luminal surface of the stent and a relatively higher concentration of sirolimus in the area of the mural or abluminal face of the stent. This configuration creates a longer path or higher resistance to elution of the drug to the luminal face areas compared to the mural or abluminal face and as such should result in substantially all of the sirolimus being delivered to the mural or abluminal side of the stent and into the arterial tissues.

The sirolimus composition within a reservoir will preferably comprise sirolimus, a bioresorbable polymer, a stabilizing agent and a solvent, wherein each of the components will be in the certain proportion relative to one another. Preferably, the total dose or amount of sirolimus available from the stent is between 0.15 and 2.7 micrograms per square millimeter of arterial tissue area, where the area of arterial tissue is defined as the area of the surface of a theoretical cylinder whose diameter and length are the diameter and length of the expanded stent as deployed in the artery. More preferably, the total dose or amount of sirolimus available from the stent is between 0.7 and 1.2 micrograms per square millimeter of arterial tissue. More preferably, the total dose or amount of sirolimus available from the stent is between 0.87 and 1.1 micrograms per square millimeter of arterial tissue. However, the release specification for this exemplary embodiment is between ninety and one hundred ten percent of the label claim, and thus the total dose or amount of sirolimus available from the stent is between 0.78 and 1.21 micrograms per square millimeter of arterial tissue As set forth above, the bioresorbable polymer utilized in the composition comprises PLGA. More preferably, the composition comprise a PLGA polymer where the molar ratio of lactide to glycolide residues (L:G) in the polymer chain is from about 100:0 to about 50:50. Even more preferably, the composition comprises a PLGA polymer where the molar ratio of lactide to glycolide residues (L:G) in the polymer chain is from about 80:20 to about 70:30. The weight ratio of sirolimus to PLGA, designated as the D:P ratio is preferably in the range from about 30/70 to about 60/40, more preferably from about 42/58 to about 50/50 and more preferably 46/54. All ratios are weight percentages. Alternatively, the relative weight proportion of sirolimus and PLGA may be expressed in a normalized form, D:P. Accordingly, the preferred D:P ratio is in the range from about 1:0.66 to about 1:2.3, more preferably from about 1:1.00 to about 1:1.38 and even more preferably about 1:1.17. The intrinsic viscosity of the polymer is 0.66 to 0.72 dL/g.

Also as described above, the sirolimus composition preferably comprises BHT, butylated hydroxy toluene or butylated hydroxytoluene. The amount of BHT added is preferably less than about 3 percent by weight of the amount of sirolimus. Even more preferably, the amount of BHT added is in the range from about 1.2 percent by weight to about 2.6 percent by weight of the amount of sirolimus. Yet even more preferably, the amount of BHT added is in the range from about 1.6 percent by weight to about 2.0 percent by weight of the amount of sirolimus.

In order to make the above-described constituents a solution for deposition purposes, a suitable solvent is required. Dimethyl sulfoxide, DMSO, is the preferred solvent and is preferably utilized in the present invention. The amount present is in the range from about 0.01 percent to about 20 percent by weight relative to the weight of sirolimus. Even more preferably, DMSO is utilized in an amount in the range from about 1 percent to about 15 percent by weight relative to the weight of sirolimus. Even yet more preferably, DMSO is utilized in an amount in the range from about 4 percent to about 12 percent by weight relative to the weight of sirolimus, and more preferably, in the range from about 7 percent to about 10 percent by weight relative to the weight of sirolimus.

It is important to note that the drug loading or doses for each drug may be expressed in any number of ways, including those set forth above. In a preferred exemplary embodiment, the dose ranges may be expressed as nested absolute ranges of drug weight based on a standard 3.5 mm×17 mm stent size. In this way, the dose ranges would scale with stent size and reservoir count. For example, in a 3.5 mm×17 mm stent size the number of holes or reservoirs is 585. In other exemplary embodiments, the number of reservoirs for a given size stent may include 211 reservoirs for a 2.5 mm×8 mm stent, 238 for a 3.0 mm×8 mm stent, 290 reservoirs for a 3.5 mm×8 mm stent, 311 reservoirs for a 2.5 mm×12 mm stent, 347 for a 3.0 mm×12 mm stent, 417 reservoirs for a 3.5 mm×12 mm stent, 431 reservoirs for a 2.5 mm×17 mm stent, 501 for a 3.0 mm×17 mm stent, 551 reservoirs for a 2.5 mm×22 mm stent, 633 for a 3.0 mm×22 mm stent, 753 reservoirs for a 3.5 mm×22 mm stent, 711 reservoirs for a 2.5 mm×28 mm stent, 809 for a 3.0 mm×28 mm stent, 949 reservoirs for a 3.5 mm×28 mm stent, 831 reservoirs for a 2.5 mm×33 mm stent, 963 for a 3.0 mm×33 mm stent and 1117 reservoirs for a 3.5 mm×33 mm stent. The load or dose of sirolimus on a 3.5 mm×17 mm stent may be in the range from about 30 micrograms to about 500 micrograms, more preferably from about 130 micrograms to about 200 micrograms and even more preferably from about 140 micrograms to about 185 micrograms. It is important to note that these are exemplary sizes and reservoir counts. As stated above, the dose ranges would scale with stent size and reservoir count. Drug weight can be adjusted upward or downward to account for negative or positive securement features to achieve the desired dose range as these features can modify the resulting available volume of the reservoir albeit in a small fashion. These doses are for the final sterilized stent product.

It is also important to note that the duration of release may also be tailored. For example, the in vivo release for sirolimus may be from about 7 to about 120 days and more preferably from about 14 to about 90 days.

For any of the exemplary embodiments described herein, the reservoir securement feature may be utilized as is explained in detail subsequently.

The exemplary stent of the present invention is very flexible and deliverable, while still providing sufficient radial strength to maintain vessel patency. The stent may be formed in any suitable manner, such as by laser cutting a tube made from a suitable material, including cobalt chromium alloys, stainless steel alloys or nickel titanium alloys. Although coronary flexible stents of the present invention are disclosed to illustrate one exemplary embodiment of the present invention, one of ordinary skill in the art would understand that the disclosed exemplary embodiment of the present invention may be equally applied to other locations and lumens in the body, such as, for example, vascular, non-vascular and peripheral vessels, ducts, and the like. As described in more detail below, the securement features themselves may be created by laser cutting or other methods such as electro-discharge machining, or even aggressive electro or chemical etching.

Reservoir eluting stents offer a number of advantages over standard surface coated drug eluting stents. For example, reservoirs protect the polymer and drug matrix or composition deposited therein from mechanical disruption during passage through the tortuous anatomy and highly calcified lesions that may cause delaminating of standard surface coated stents. Reservoirs allow higher drug loading capacity and higher drug to polymer ratios because the polymers in the reservoir are not subject to the elongation and deformation associated with polymer surface coatings. Reservoirs also require less polymer mass than conventional surface coatings and can reduce strut thickness by ten to thirty microns thereby improving both the flexibility of the stent as well as reducing the overall profile of the device. Reservoirs also make it easier to deliver multiple drugs and or therapeutic agents from a stent with independent release profiles and to treat the metallic surfaces of the stent without affecting its drug and polymer attributes. Furthermore, reservoirs provide greater flexibility and options as it relates to providing selective directional delivery and positional and/or directional localized delivery. In addition, reservoirs may offer better vessel biocompatibility by providing a stent surface that is predominantly bare metal with virtually no polymer contacting the vessel wall on implantation. This is true given the meniscus of the composition within the reservoirs and the less than complete filling of the available reservoir as is explained in detail subsequently. By incorporation of a fixation feature in accordance with the present invention, one can secure and maintain the fixation of the therapeutic agent inlay to that of the reservoir for the complete service life of the stent, or in cases of absorbable or resorbable inlays, until the therapeutic agent inlay is completely absorbed or resorbed. During delivery of the stent to the targeted area and upon deployment of the stent, the stent and resulting inlays may be subject to loading and deformations which may impact the fixation of the drug inlay. The use of features in the reservoirs may provide an additional level of fixation resulting in the inlay being securely fixed and remain being fixed throughout the service life of the stent even in the most severe loading regimes that a stent may undergo.

Bare metal stents offer advantages as well as briefly described above. The reservoir eluting stents of the present invention combine the best features of bare metal stents with those of drug eluting stents. In the exemplary embodiments described herein, the reservoir eluting stents are approximately seventy-five percent bare metal and twenty-five percent polymer and drug on or proximate to its outer or abluminal surface. If the reservoirs are less than full and they are filled such that the layers or inlays start from the luminal side as described above, then the reservoir eluting stents are seventy-five percent bare metal and twenty-five open reservoir surface area relative to the abluminal surface. In other words, of the entire surface area of the stent on its outer surface, approximately twenty-five percent is the area of the reservoirs while the remaining seventy-five percent is the surface area of the struts and hinges. These percentages are initial values. In other words, at the time of implantation of the stent, seventy-five percent of the stent surface area contacting the vessel wall is bare metal and twenty-five percent of the surface area of the stent is reservoirs at least partially filled with polymer and drug as is explained in detail subsequently. However, as the PLGA is biodegradable via hydrolysis of its ester linkages, at approximately ninety days, there is no longer any polymer and/or drug left in the reservoirs of the stent. Accordingly, at ninety days, one hundred percent of the stent is bare metal, the reservoirs having been depleted of the drug and polymer contained therein. More specifically, the entire surface area of the stent exposed to the vessel is bare metal and there is no polymer and/or polymer and drug left in the reservoirs. Therefore, with the drug delivered, restenosis is eliminated and the bare metal stent is left behind as scaffolding to prevent recoil. With this design, one achieves the benefit of a bare metal stent; namely, reduced potential risk of thrombosis and/or emboli and the anti-restenotic effects of local drug delivery.

As set forth above, each exemplary stent comprises a plurality of reservoirs that are filled or at least partially filled with the mixture of sirolimus (a rapamycin), PLGA polymer and BHT (antioxidant). Each individual reservoir comprises substantially the same amount of the mixture. In order to achieve both the desired dose of sirolimus and the desired elution rate or kinetic release profile of sirolimus from the stent once placed in the artery of a patient, a specific ratio of the weight amount each of sirolimus, PLGA and BHT (called the "formulation") must be deposited into the stent reservoirs. Each reservoir has present a securement feature to ensure that upon solidification of the construct or inlay that the construct or inlay remains securely attached to the device. The dose rates and release kinetics are described above. It is only required that the available total volume of all the reservoirs in the stent, and by extension the available volume in each individual reservoir in the stent, be equal to or greater than the total volume required by the formulation that will provide the desired benefit to the patient. In fact, if the required amount of formulation which may equally accurately be expressed as a volume of formulation is less than the total volume available, then less than the total volume of the stent reservoir will be filled with the desired amount of formulation. In fact, for the exemplary device of the present invention, a lesser volume than the total available volume is required for an efficacious stent product. Preferably the percent proportion of the total available reservoir volume that is occupied by the formulation will be between forty percent and seventy percent of the total available volume, and more preferably between fifty percent and sixty-one percent of the total available volume.

Figure 4:
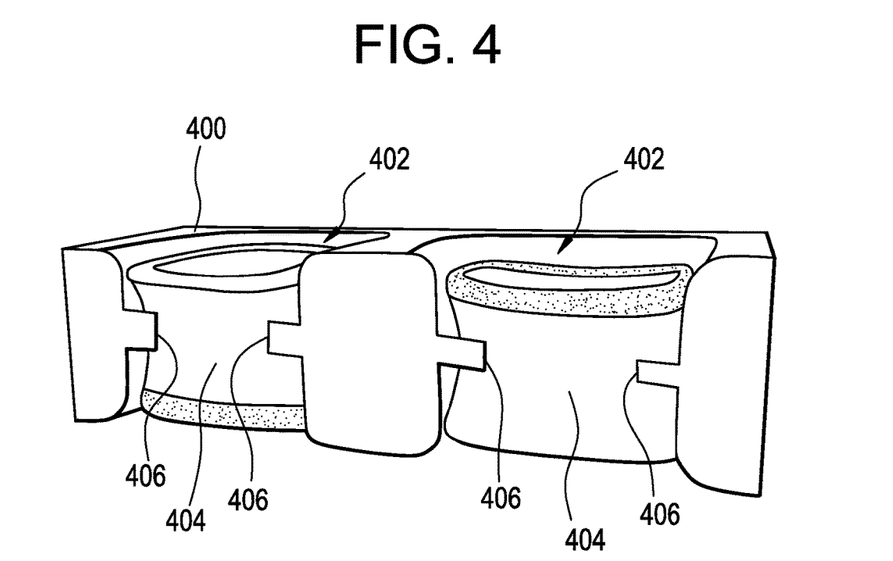
FIG. 4 is a diagrammatic, side view representation of a portion of a drug eluting stent wherein the side walls of the reservoir incorporate a positive feature that interlocks with the inlay constructs in accordance with the present invention.

FIG. 4 diagrammatically illustrates an exemplary embodiment of the present invention, wherein the drug reservoirs 402 of a stent 400 comprise drug or therapeutic agent constructs or inlays 404 that are further secured within the reservoir 402 by securement features 406. It is important to note that the drug or therapeutic agent construct will preferably adhere to the walls of the reservoirs 402 which is the primary mode of retention, while the securement feature adds an extra mechanical interlock means of retention. Although a single pair of securement features 406 are shown for each drug construct 404, there may be multiple securement features present throughout the height of the reservoir 402, or alternatively securement feature 406 may be in the form of one or more continuous rings around the periphery of the reservoir 402, located centrally, towards the bottom, and/or located towards the top of the reservoir 402. The securement features 406 may comprise any suitable material and may be attached in any suitable manner; however, in the preferred embodiment, the features are machined from the stent 400 itself.

Figure 5:
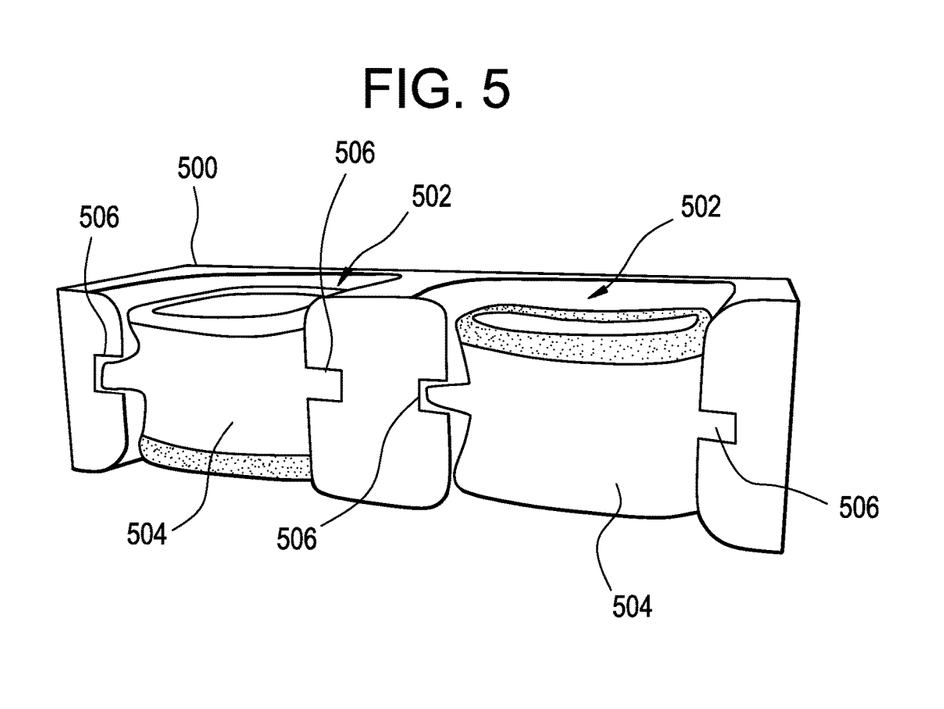
FIG. 5 is a diagrammatic, side view representation of a portion of a drug eluting stent wherein the side walls of the reservoir incorporate a negative feature that interlocks with the inlay constructs in accordance with the present invention.

While FIG. 4 illustrates the securement feature 406 protruding into the drug construct 404 to secure the drug construct 404 in the reservoir 402, FIG. 5 illustrates an alternative exemplary embodiment wherein drug reservoir 502 comprises drug construct 504 secured by securement feature 506. In this exemplary embodiment, the securement feature 506 is a recess in the wall of reservoir 502 of the stent 500 in contrast to the protrusion 406 as shown in FIG. 4. Once again, securement feature 506 may be present in multiple locations, and/or in the form of a continuous groove around the wall of reservoir 502 or at discreet locations on the vertical wall of the reservoir 502.

Figure 6:
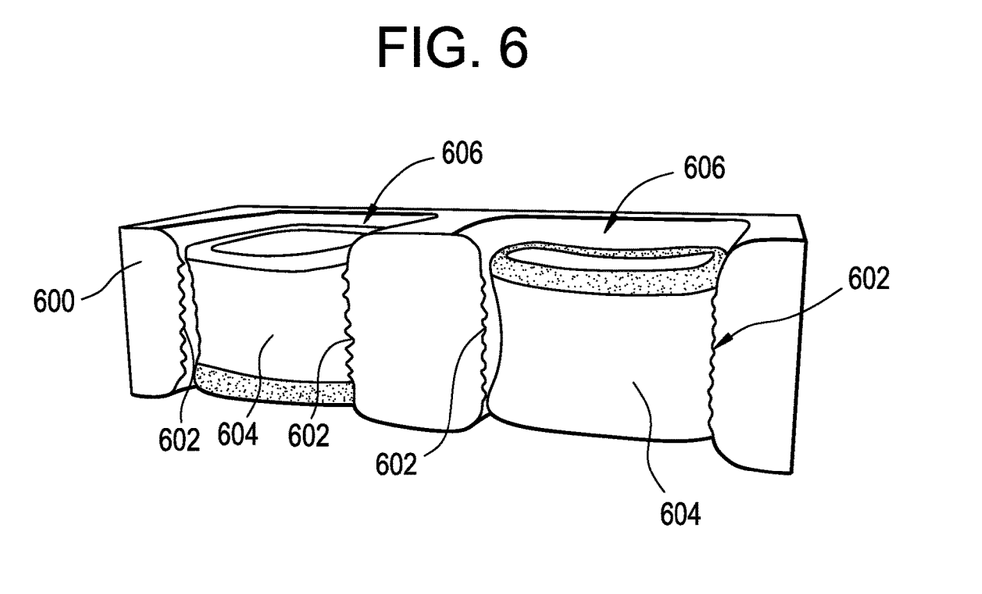
FIG. 6 is a diagrammatic, side view representation of a portion of a drug eluting stent wherein the side walls of the reservoir have an aggressive macro-surface texture feature that facilitates interlocking with the inlay constructs in accordance with the present invention.

FIG. 6 illustrates a securement feature 602 in the form of a roughened surface which may have macro or micro texturing to secure drug construct or inlay 604 within reservoirs 606 of the stent 600. Such texturing may be created by mechanical removal of material such as by localized grit-blasting, or by localized etching with chemical agents and appropriate masking of surfaces where such features are not desired, resulting in an micro-textured surface. In cases of macro-texturing, larger grit sizes may be employed, or alternative cutting tools may be utilized to create a non-planar surface along the wall. The use of water jets or laser cutting may also be employed to create said securement feature 602. Any suitable mechanical, electrical and/or chemical means may be utilized to create the securement feature 602.

Figure 7:
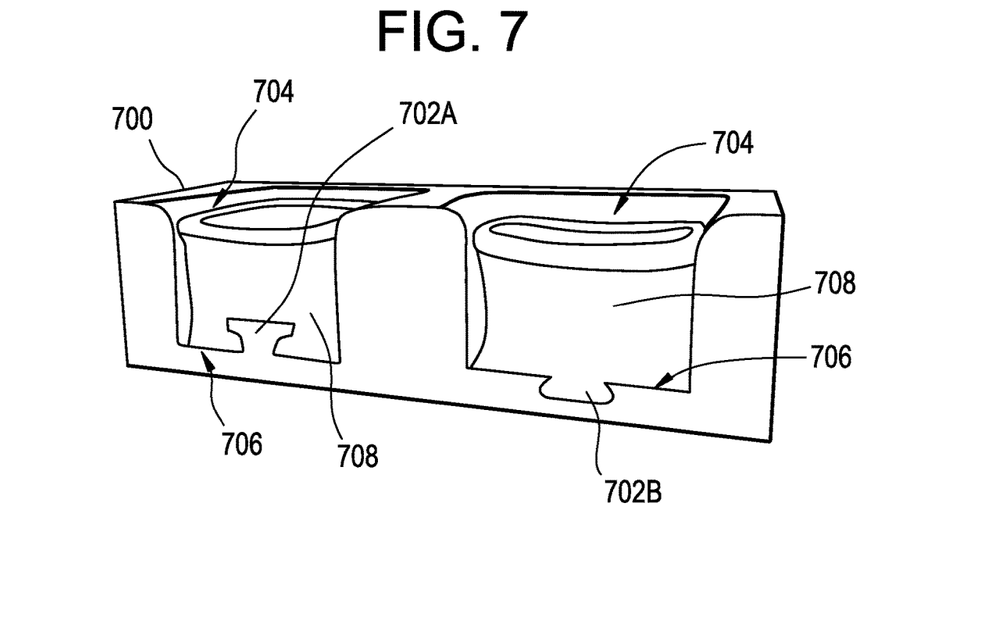
FIG. 7 is a diagrammatic, side view representation of a portion of a drug eluting stent in wherein the reservoir bottom is shown with both the positive and negative interlock feature in accordance with the present invention.

FIG. 7 illustrates securement features 702A and 702B this time located at the base of the reservoir 704. In this exemplary embodiment, the reservoirs 704 of the stent 700 do not extend through the entire thickness of the device, resulting in the presence of a base 706 of reservoir 704. Drug construct 708 may be secured by a positive securement feature 702A or by a negative securement feature 702B, or a combination of both. The securement features 702A and 702B located on the base 706 may be used independently or in combination with additional securement features located on the vertical walls. Although a dovetail shape is shown, any geometry which provides a secure interlocking of the construct 708 upon curing to that of the reservoir 704 may be utilized. The shape may be drilled, bored or created by EDM (Electro-discharge machining). Essentially, any suitable means may be utilized to create the securement element.

Figure 8A:
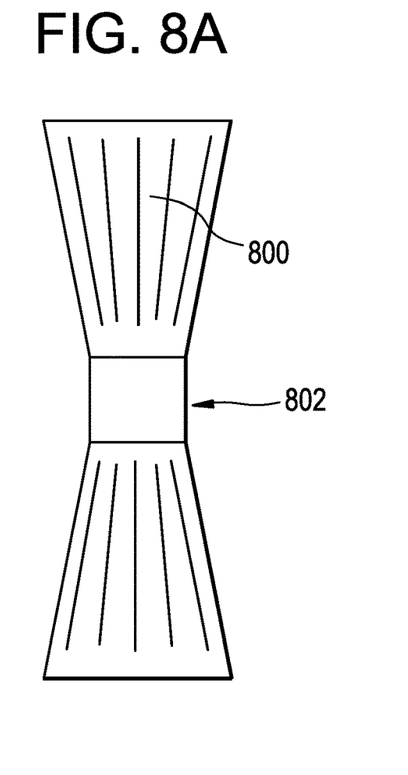
FIGS. 8a and 8b include a diagrammatic view showing a typical laser beam and the resulting laser beam waist, and how this may be leveraged to create features as shown in FIG. 8b in accordance with the present invention.
Figure 8B:
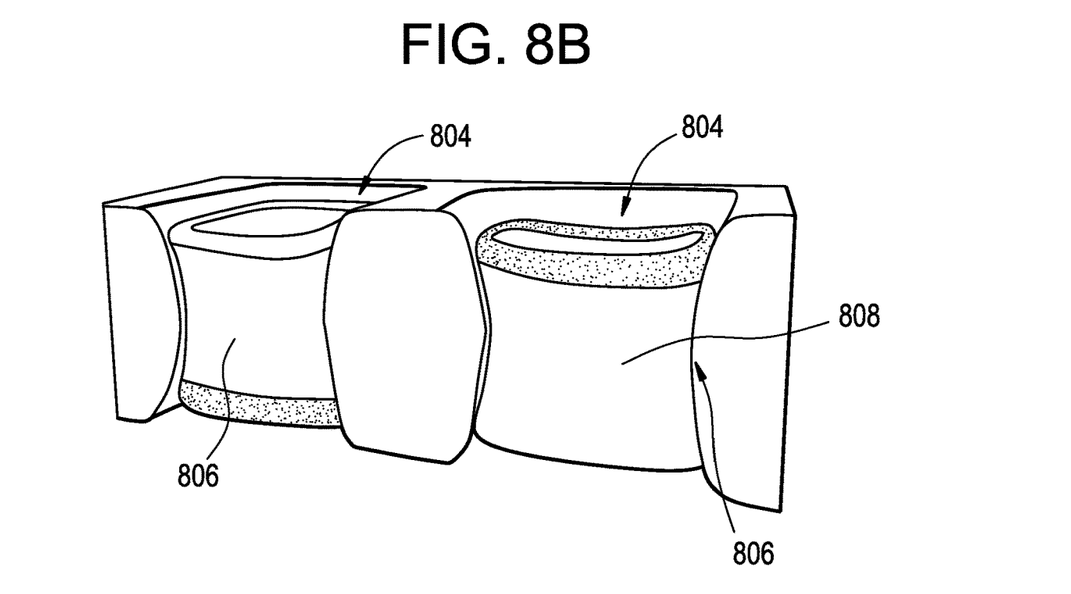

FIG. 8A schematically illustrates a portion of a typical laser beam 800 having a beam waist 802. Typically the intensity of the laser beam 800 is greatest at the beam waist 802. It is the area where the beam 800 is the smallest, and the focusing of the beam 800 may alter the shape and height of the beam waist 802. This principle may be leveraged to create reservoirs which when cutting with a laser beam of appropriate laser beam waist parameters may result in a drug reservoir 804 with securement features 806 as illustrated in FIG. 8B to ensure retention and securement of drug construct 800 in drug reservoir 804. The resulting geometry of securement feature 806 may also be achieved by angling the longitudinal axis of the laser itself relative to the longitudinal axis of the reservoir 804. It is important to note that in this exemplary embodiment, the feature 808 is the shape of the reservoir wall, which in this embodiment is currently an hour-glass shape. A reverse hour glass shape may also be utilized by appropriate use of the laser beam. In addition, any shape that would prevent movement of the construct in either direction would serve as a securement means.

Each of the above described exemplary embodiments may be utilized alone or in combination to aid in retaining the drug or therapeutic agent constructs within the reservoirs. As stated above, the primary mechanism of retention is adhesion to the walls. The secondary securement mechanisms provide an additional means of securement or anchor points. In the case of hour glass shaped reservoirs, the shape prevents movement of the construct in any one direction so that it cannot move in either direction.

Proper securement of the construct or inlay within each reservoir ensures that the drug or therapeutic agent is available for elution within the body. A stent undergoes various loading conditions which may cause inlays or constructs to become dislodged and separate from the device. The present invention serves to prevent this from occurring.

Although shown and described is what is believed to be the most practical and preferred embodiments, it is apparent that departures from specific designs and methods described and shown will suggest themselves to those skilled in the art and may be used without departing from the spirit and scope of the present invention. The present invention is not restricted to the particular constructions described and illustrated, but should be construed to cohere with all modifications that may fall within the scope of the appended claims.

What is claimed is:

1. A bare metal stent with drug eluting reservoirs for implantation into a tubular organ of a living organism comprising:

an elongated, substantially tubular structure having a luminal surface and an abluminal surface, the elongated, substantially tubular structure including a plurality of interconnected elements, a portion of which comprise at least one reservoir formed within the tubular structure;

at least one retention and securement feature operatively associated with the at least one reservoir, wherein the at least one retention and securement feature has a top surface and a bottom surface, and wherein the at least one reservoir has an opening at the luminal surface and an opening at the abluminal surface and wherein the at least one reservoir is defined by interior surfaces separate from the openings, such that the at least one retention and securement feature is positioned at an intermediate location along the interior surface of the at least one reservoir between the luminal surface and the abluminal surface of the tubular structure; and an inlay, including at least one of a polymer and therapeutic agent, positioned within the at least one reservoir, the at least one retention and securement feature extending into the inlay such that at least a portion of the inlay is positioned between the top surface of the at least one retention and securement feature and between the luminal surface and the bottom surface of the at least one retention and securement feature and the abluminal surface of the tubular structure, the at least one retention and securement feature anchoring the inlay within the at least one reservoir.

2. The bare metal stent according to claim 1, wherein the at least one reservoir extends from the luminal surface to the abluminal surface.

3. The bare metal stent according to claim 2, wherein the at least one retention and securement feature comprises a protrusion from the interior surface of the reservoir into the reservoir.

4. The bare metal stent according to claim 2, wherein the at least one retention and securement feature comprises a recess within the inner surface of the reservoir.

5. The bare metal stent according to claim 2, wherein the at least one retention and securement feature comprises a texture on the interior surface of the reservoir.

6. The bare metal stent according to claim 1, wherein the at least one reservoir partially extends from at least one of the abluminal surface to luminal surface or from the luminal surface to the abluminal surface thereby creating a reservoir bottom.

7. The bare metal stent according to claim 6, wherein the at least one retention and securement feature comprises a protrusion extending from the interior surface corresponding to the reservoir bottom.

8. The bare metal stent according to claim 6, wherein the at least one retention and securement feature comprises a recess formed in the interior surface corresponding to the reservoir bottom.

* * * * *